US00PP10966P

United States Patent [19]

Rother

[11] Patent Number: Plant 10,966

[45] Date of Patent: Jun. 22, 1999

[54] SUTERA PLANT NAMED 'BLIZZARD'

[76] Inventor: Reinhard W. Rother, 56 Emerald Monbulk Road, Emerald, Victoria, 3782, Australia

[21] Appl. No.: 08/977,480

[22] Filed: Nov. 24, 1997

[51] Int. Cl.[6] ..... A01H 5/00

[52] U.S. Cl. ..... Plt./263

[58] Field of Search ..... Plt./68.1

*Primary Examiner*—Elizabeth Kemmerer

*Attorney, Agent, or Firm*—C. A. Whealy

[57] ABSTRACT

A distinct cultivar of Sutera plant named 'Blizzard', characterized by its prostrate to trailing growth habit; vigorous and rapid growth rate; numerous large white flowers that flower for a long period of time; broad, cordate foliage that is fragrant; resistance to bacterial and fungal pathogens common to Suteras; and heat tolerance.

1 Drawing Sheet

The present invention relates to a new and distinct cultivar of Sutera plant, botanically known as *Sutera cordata*, and hereinafter referred to by the cultivar name Blizzard. It is proposed that the new Sutera will be marketed under the name Snowstorm.

The new Sutera was discovered by the inventor in a controlled environment in Emerald, Australia, in March, 1995, as a naturally-occurring mutation of the *Sutera cordata* cultivar Snowflake (not patented). The new Sutera was observed as a single plant that was more vigorous, had larger and more numerous flowers, flowered for a longer period of time and had broader leaves. In addition, plants of the new Sutera are more resistant to bacterial and fungal pathogens common to Suteras, more heat tolerant and have fragrant foliage compared to plants of the parent cultivar Snowflake.

Asexual reproduction of the new Sutera by terminal cuttings taken at Emerald, Australia, has shown that the unique features of this new Sutera are stable and reproduced true to type in successive generations.

The cultivar Blizzard has not been observed under all possible environmental conditions. The phenotype may vary somewhat with variations in environment such as temperature, light intensity, and fertility level, without, however, any variance in genotype.

The following traits have been repeatedly observed and are determined to be the unique characteristics of 'Blizzard'. These characteristics in combination distinguish 'Blizzard' as a new and distinct cultivar:

1. Prostrate to trailing growth habit.
2. Vigorous and rapid growth rate.
3. Numerous large white flowers that flower for a long period of time.
4. Broad, cordate foliage that is fragrant.
5. Resistance to bacterial and fungal pathogens common to Suteras.
6. Heat tolerance.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. The photograph comprises a side perspective view of a typical hanging basket plant of the cultivar Blizzard. Flower and foliage colors in the photograph may appear different than the actual colors due to light reflectance.

DETAILED BOTANICAL DESCRIPTION

The following observations and measurements describe plants grown during the spring and summer in Encinitas, Calif. under full sun with day and night temperatures averaging 24° and 16° C., respectively. Color references are made to The Royal Horticultural Society Colour Chart except where general terms of ordinary dictionary significance are used.

Botanical classification: *Sutera cordata* cultivar Blizzard.

Parentage: Naturally-occurring mutation of the *Sutera cordata* cultivar Snowflake (not patented).

Propagation:

*Type*.—By cuttings.

*Time to initiate roots*.—7 to 10 days at temperatures of 20° C.

*Time to develop roots*.—18 to 24 days at temperatures of 20 to 25° C.

*Rooting habit*.—Vigorous, numerous and fine.

Plant description:

*Form*.—Prostrate and trailing, vigorous herbaceous annual.

*Branching habit*.—Freely branching, multiple branches with secondary laterals.

*Plant height*.—About 9.5 cm.

*Plant diameter*.—About 1.3 meters.

*Vigor*.—Excellent, high.

*Lateral stem description*.—Wiry, creeping. Internode length: About 2.8 cm. Diameter: About 1 mm. Texture: Slightly pubescent. Color: 143C.

*Foliage description*.—Leaves single, opposite and generally symmetrical. Usually about 20 leaves per lateral branch. Foliage fragrant. Length: About 2 cm. Width: About 1.9 cm. Shape: Broadly cordate. Apex: Broadly acute. Base: Rounded. Margin: Serrate. Texture: Slightly pubescent on both surfaces. Color: Young leaves, upper surface: 144A. Young leaves, lower surface: 144A. Mature leaves, upper surface: 146A. Mature leaves, lower surface: 146B. Venation, upper surface: 146A. Venation, lower surface: 146B. Petiole: Length: About 8 mm. Diameter: Less than 0.1 mm. Color: 144A.

Flower description:

*Flower type and habit*.—Flowers solitary and axillary, usually two per node. Flowers salverform, sympetalous, actinomorphic with slender corolla tube abruptly flared to five flat lobes. Floriferous, but flowers only formed on new growth, usually about 20 flowers per lateral branch. Flowers persistent.

*Natural flowering season*.—Spring through fall.

*Fragrance*.—None.

*Flower size*.—Length: About 1 cm. Diameter: About 1.3 cm. Corolla tube diameter: About 2 mm.

*Corolla*.—Appearance: Smooth, very tiny hairs on back side. Aspect: Flat. Lobe length: About 6 mm. Lobe width: About 4 mm. Lobe shape: Rounded. Margin: Entire. Color: When opening, upper surface: 155D, slightly off-white. When opening, lower surface: 158A, slightly creamy. Fully opened, upper surface: White. Fully opened, lower surface: Lobes, white, base of corolla tube, slightly yellowish, 160A.

*Peduncle*.—Angle: Acute. Strength: Slender and flexible, but strong enough to support flower upright. Length: About 5 mm. Color: 144A.

*Flower bud*.—Shape: Tubular, elongated. Length: About 6 mm. Diameter: About 1 mm. Color: 145C.

*Calyx*.—Shape: Five-parted tube fused at base. Length: About 8 mm. Diameter: About 2.5 mm. Sepal shape: Linear, narrow. Sepal apex: Narrowly acute. Sepal margin: Entire. Sepal texture: Very slightly hirsute. Color, both surfaces: 144A.

*Reproductive organs*.—Androecium: Stamen number: Four. Stamen shape: Kidney-shaped. Anther size: Less than 0.5 mm. Anther color: 12A. Amount of pollen: Low. Pollen color: 12A. Gynoecium: Pistil length: About 9 mm. Stigma shape: Curved, club-like. Style length: About 8 mm. Style color: 1B. Stigma color: 1B. Ovary color: 144A.

Disease resistance: The new Sutera has been observed to be more resistant to bacterial and fungal pathogens common to Suteras.

Temperature tolerance: The new Sutera has been observed to be more high temperature tolerant than other cultivars of Sutera.

Seed production: Seed production has not been observed.

It is claimed:

1. A new and distinct cultivar of Sutera plant named 'Blizzard', as illustrated and described.

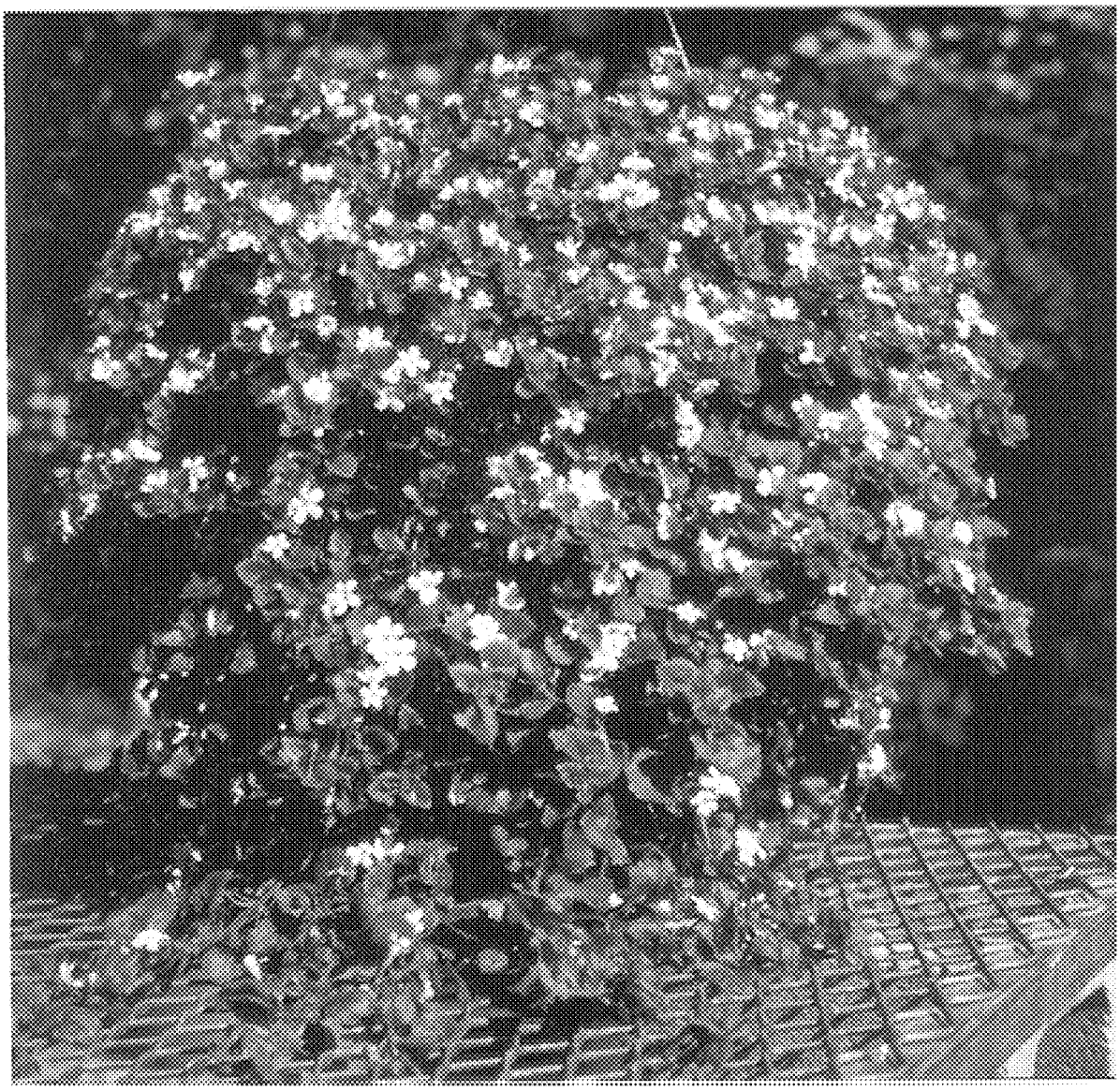

* * * * *